United States Patent
Beach et al.

(10) Patent No.: US 9,424,634 B2
(45) Date of Patent: *Aug. 23, 2016

(54) MACHINE VISION SYSTEM FOR IDENTIFYING AND SORTING PROJECTILES AND OTHER OBJECTS

(71) Applicant: Cybernet Systems Corporation, Ann Arbor, MI (US)

(72) Inventors: Glenn J. Beach, Grass Lake, MI (US); Gary Moody, Dexter, MI (US); James Burkowski, Northville, MI (US); Charles J. Jacobus, Ann Arbor, MI (US)

(73) Assignee: Cybernet Systems Corporation, Ann Arbor, MI (US)

(*) Notice: Subject to any disclaimer, the term of this patent is extended or adjusted under 35 U.S.C. 154(b) by 644 days.

This patent is subject to a terminal disclaimer.

(21) Appl. No.: 13/834,909

(22) Filed: Mar. 15, 2013

(65) Prior Publication Data

US 2015/0254828 A1 Sep. 10, 2015

Related U.S. Application Data

(63) Continuation-in-part of application No. 11/072,599, filed on Mar. 4, 2005, now abandoned.

(60) Provisional application No. 60/550,188, filed on Mar. 4, 2004.

(51) Int. Cl.
| | |
|---|---|
| G06K 9/00 | (2006.01) |
| G06T 7/00 | (2006.01) |
| B07C 5/34 | (2006.01) |
| G01N 21/88 | (2006.01) |

(Continued)

(52) U.S. Cl.
CPC ............. *G06T 7/0004* (2013.01); *B07C 5/34* (2013.01); *G01N 21/8851* (2013.01); *G01N 21/952* (2013.01); *G01N 2021/845* (2013.01); *G06K 2209/19* (2013.01); *G06T 2207/30108* (2013.01); *G06T 2207/30164* (2013.01)

(58) Field of Classification Search
CPC ............. G06T 2207/301108; G06T 7/0004
See application file for complete search history.

(56) References Cited

U.S. PATENT DOCUMENTS

| | | |
|---|---|---|
| 2,422,036 A | 6/1947 | Oakley |
| 3,813,174 A | 5/1974 | Nowak et al. |

(Continued)

FOREIGN PATENT DOCUMENTS

| | | |
|---|---|---|
| JP | 3879007 | 3/1999 |
| WO | WO-92/20988 | 11/1992 |
| WO | WO-2005022076 | 3/2005 |

OTHER PUBLICATIONS

ATK—An Advanced Weapon and Space Systems Company, Reaching New Frontiers. http://www.atk.com.

*Primary Examiner* — Gregory M Desire
(74) *Attorney, Agent, or Firm* — Dinsmore & Shohl LLP

(57) ABSTRACT

A machine vision system for automatically identifying and inspecting objects is disclosed, including composable vision-based recognition modules and a decision algorithm to perform the final determination on object type and quality. This vision system has been used to develop a Projectile Identification System and an Automated Tactical Ammunition Classification System. The technology can be used to create numerous other inspection and automated identification systems.

35 Claims, 18 Drawing Sheets

(51) Int. Cl.
*G01N 21/952* (2006.01)
*G01N 21/84* (2006.01)

(56) References Cited

U.S. PATENT DOCUMENTS

| | | | |
|---|---|---|---|
| 3,902,811 A | 9/1975 | Altman et al. | |
| 4,163,212 A | 7/1979 | Buerger et al. | |
| 4,271,967 A | 6/1981 | Matsuo et al. | |
| 4,281,583 A | 8/1981 | Pollock et al. | |
| 4,457,622 A | 7/1984 | Kato et al. | |
| 4,503,557 A | 3/1985 | Maeda | |
| 4,589,141 A | 5/1986 | Christian et al. | |
| 4,696,047 A | 9/1987 | Christian et al. | |
| 4,706,120 A | 11/1987 | Slaughter et al. | |
| 4,755,753 A | 7/1988 | Chern | |
| 4,831,251 A | 5/1989 | Hanna | |
| 4,831,741 A | 5/1989 | Sogoian | |
| 4,923,066 A | 5/1990 | Ophir et al. | |
| 4,980,119 A | 12/1990 | Schoenig, Jr. et al. | |
| 5,062,532 A | 11/1991 | Zivley | |
| 5,142,591 A | 8/1992 | Baird et al. | |
| 5,150,426 A | 9/1992 | Banh et al. | |
| 5,157,486 A | 10/1992 | Baird et al. | |
| 5,273,166 A | 12/1993 | Sawamura | |
| 5,311,977 A | 5/1994 | Dean et al. | |
| 5,383,021 A | 1/1995 | Hanna | |
| 5,443,419 A | 8/1995 | Adams et al. | |
| 5,568,263 A | 10/1996 | Hanna | |
| 5,608,530 A | 3/1997 | Gates | |
| 5,699,447 A * | 12/1997 | Alumot et al. | 382/145 |
| 5,799,105 A | 8/1998 | Tao | |
| 5,812,693 A | 9/1998 | Burt et al. | |
| 5,974,169 A | 10/1999 | Bachelder | |
| 5,978,502 A | 11/1999 | Ohashi | |
| 6,040,900 A | 3/2000 | Chen | |
| 6,043,870 A | 3/2000 | Chen | |
| 6,122,001 A | 9/2000 | Micaletti et al. | |
| 6,173,066 B1 | 1/2001 | Peurach et al. | |
| 6,252,661 B1 | 6/2001 | Hanna | |
| 6,285,034 B1 | 9/2001 | Hanna et al. | |
| 6,313,948 B1 | 11/2001 | Hanna | |
| 6,360,895 B1 | 3/2002 | Riggenmann et al. | |
| 6,448,549 B1 | 9/2002 | Safaee-Rad | |
| 6,496,598 B1 | 12/2002 | Harman | |
| 6,501,554 B1 | 12/2002 | Hackney et al. | |
| 6,522,777 B1 | 2/2003 | Paulsen et al. | |
| 6,584,805 B1 | 7/2003 | Burns et al. | |
| 6,610,953 B1 * | 8/2003 | Tao | B07C 5/342 209/11 |
| 6,618,495 B1 | 9/2003 | Furnas | |
| 6,687,398 B1 | 2/2004 | Kriwet et al. | |
| 6,701,001 B1 * | 3/2004 | Kenneway | B07C 5/3422 382/141 |
| 6,714,671 B1 | 3/2004 | Wakitani et al. | |
| 6,714,679 B1 | 3/2004 | Scola et al. | |
| 6,748,104 B1 | 6/2004 | Bachelder et al. | |
| 6,801,637 B2 | 10/2004 | Voronka et al. | |
| 6,805,245 B2 * | 10/2004 | Kenneway | 209/538 |
| 6,822,181 B2 | 11/2004 | Linton | |
| 6,831,996 B1 | 12/2004 | Williams et al. | |
| 6,856,698 B1 | 2/2005 | Silver et al. | |
| 6,930,690 B1 | 8/2005 | Kulkarni | |
| 6,959,108 B1 | 10/2005 | Bartelt et al. | |
| 7,061,604 B1 | 6/2006 | Beam et al. | |
| 7,403,872 B1 * | 7/2008 | St. Onge et al. | 702/185 |
| 8,297,446 B2 | 10/2012 | Spence, Jr. | |
| 8,983,173 B2 * | 3/2015 | Beach et al. | 382/141 |
| 2003/0053713 A1 * | 3/2003 | Romanik | G06T 7/0004 382/284 |
| 2003/0057137 A1 | 3/2003 | Wojtecki et al. | |
| 2003/0063281 A1 * | 4/2003 | Katane et al. | 356/427 |
| 2003/0167616 A1 * | 9/2003 | Harding | B23P 6/002 29/407.05 |
| 2004/0156539 A1 | 8/2004 | Jansson et al. | |
| 2005/0111726 A1 * | 5/2005 | Hackney | G01B 11/2513 382/145 |
| 2005/0174567 A1 | 8/2005 | Hanna | |
| 2006/0022669 A1 | 2/2006 | Nygaard | |
| 2006/0152589 A1 * | 7/2006 | Morrison et al. | 348/208.1 |
| 2006/0236792 A1 | 10/2006 | Hanna | |
| 2007/0117225 A1 | 5/2007 | Capaldo et al. | |
| 2012/0012509 A1 | 1/2012 | Spence, Jr. | |
| 2015/0178913 A1 * | 6/2015 | Beach et al. | 382/141 |

* cited by examiner

Example:

Red or Orange for Tracers

Green of No Color for Normal Ball Ammunition

Corrosion

MACHINE VISION SYSTEM FOR IDENTIFYING AND SORTING PROJECTILES AND OTHER OBJECTS

REFERENCE TO RELATED APPLICATIONS

This application is a continuation-in-part of U.S. patent application Ser. No. 11/072,599, filed Mar. 4, 2005, which claims priority from U.S. Provisional Patent Application Ser. No. 60/550,188, filed Mar. 4, 2004, the entire content of both of which is incorporated herein by reference.

GOVERNMENT SUPPORT

This invention was made with Government support under Contract No. DAAE30-03-C-1060 awarded by the United States Army. The Government has certain rights in the invention.

FIELD OF THE INVENTION

This invention relates to automated inspection and, in particular, to a composable machine-vision system for identifying and inspecting ordnance, ammunition, and other objects.

BACKGROUND OF THE INVENTION

The ability to automatically identify and inspect objects is important for controlling manufacturing processes, automating processes, and reducing tedious tasks that must be performed by humans. Specialized applications-specific machine vision systems have been historically employed for such systems.

U.S. Pat. No. 4,163,212 to Buerger et al. describes a pattern recognition system which was designed in the late 1970's that used video imagers to recognize the position and orientation of an integrated circuit so as to control a wire bonding machine operation. U.S. Pat. No. 6,748,104 to Bachelder et al. describes a similar system that identifies the position of semiconductor and inspects it based on correlation between images and model patterns (edges, corners or other templates).

U.S. Pat. Nos. 4,696,047 and 4,589,141 to Christian et al. describe systems which were built beginning in the early 1980's that used computer vision-based inspection technology for dedicated inspection applications (U.S. Pat. No. 4,696,047, inspection of electrical connectors and U.S. Pat. No. 4,589,141, inspection of printed labels). U.S. Pat. No. 4,706,120 to Slaughter et al. describes a modular vision system built in the early 1980s that was based on earlier ones built by some of the inventors of the system that is the subject of this patent disclosure. It supported various dedicated inspection applications like those previous described. At this time, modular meant that the system could be included in a larger system as a module.

U.S. Pat. Nos. 5,142,591 and 5,157,486 to Baird et al. describe a system for imaging the silhouette of an ammunition object using a line scan camera and counter to reduce data rate to a microprocessor that implements silhouette boundary inspection of the object as it moves down the conveyer. U.S. Pat. No. 5,311,977 to Dean et al. describes a similar system that singulates objects on a conveyor system and images them using a high-resolution line scan CCD camera. Object images are converted via a camera synchronized counter to a silhouette are compared to reference silhouettes to effect inspection. These disclosures were less focused on the boundary-based inspection algorithm and more on employing specialized preprocessor counter hardware to reduce the computation expense of finding boundary edges in the line scan camera output serial stream.

U.S. Pat. No. 5,608,530 to Gates describes a system for acquiring an object silhouette by employing a laser backlight and measurement of the unobstructed portion of radiation-which has passed the radially opposed halves of the part under measurement. General Inspection, Inc has applied this sensor approach to ammunition inspection and screw inspection. U.S. Pat. No. 5,978,502 to Ohashi describes a system that inspects objects like solder bumps (on a printed circuit card) by comparing range data measured by a sensor to range data representing a good part U.S. Pat. Nos. 6,040,900 and 6,043,870 to Chen described laser-based imaging system that use sherography and interferometry to form images of precision surface smoothness variations which are related to materials defects in composite materials. U.S. Pat. No. 6,122,001 to Micaletti et al. describes a system that uses laser illumination imaged through a camera system to triangulate the top of packages, which is then used to focus a camera for the purpose of reading package addresses and ultimately automating package sorting.

U.S. Pat. No. 6,448,549 to Safaee-Rad describes a bottle inspection system that determines the quality of threads by capturing a video image, finding the bottleneck, and then assessing thread quality by analyzing the white/dark texture pattern to determine if they resemble bottle threads. U.S. Pat. No. 6,584,805 to Burns et al. describes a inspection machine that extracts simple features from the image of a bottle such as bottle diameter to inspect bottle just after hot molding. U.S. Pat. No. 6,618,495 to Funas describes an inspection machine for back-lit transparent containers that uses a camera to capture an image which is compared by computer to a good container template image (means for defining on said illumination area light intensities varying between the extremes of black and a maximum brightness level on said light source illumination area).

U.S. Pat. No. 6,801,637 to Voronka et al. describes a specialized computer vision system that tracks active light emitters in three line cameras to acquire movement of multiple body positions. The position of each emitter on the body is located through triangulation based on the where the emitter falls along each of the three linear cameras. The system is calibrated by moving a selected light emitter to one or several known position in the movement measurement volume. One calibrated during manufacturing the system retains calibration indefinitely. U.S. Pat. No. 6,831,996 to Williams et al. describes an apparatus that inspects automobile wheels using illumination and a zoom control camera system that acquires wheel reference features (as an example given the milled hole for a valve stem) to determine orientation and then performs inspection by assessing whether the features are in the correct position.

Comparing image derived features to model features expressed at two-dimensional patterns or boundaries has been done in both two and three dimensions for defect detection. However, generally these algorithms have been development specifically for part handling or specific part inspection. U.S. Pat. No. 6,173,066 to Peurach et al. describes a vision processing system that uses a specific approach to pattern recognition of three-dimensional objects or parts from CAD-type templates, matched in multiple views. This system does no initially understand what it is likely to see or in what particular orientation so it describes a staged approach, which hypothesizes object, position and orientation, and follows this up with boundary oriented matching procedure between edges acquired from 3 dimensional images and 3D boundaries defined by the 3D CAD-template. The cameras that take the object images are calibrated through recognition of a calibration object of known shape and size. One calibrated during manufacturing the system retains calibration indefinitely.

U.S. Pat. No. 6,687,398 to Kriwet et al. discloses a method and device for the identification of incorrectly orientated parts and/or parts departing from a predetermined master, the parts being moved by means of a conveyor means past at least one camera for registering the shapes of the parts. U.S. Pat. No. 6,822,181 to Linton describes a part diverter system which might work with a system like Peurach or Kriwet. He describes the use of an actuated paddle to divert an object from an inspection stream (pathway on a conveyor).

U.S. Pat. No. 6,714,671 to Wakitani et al. describes a system that uses model boundary matching to image derived boundaries for inspection of wiring patterns of semiconductors, printed circuit boards, or printed/impressed patterns. U.S. Pat. No. 6,714,679 to Scola et al. describes a boundary analysis technique that determines defects of a boundary to sub-pixel precision and an embodiment for fast correlation scoring for this technique. U.S. Pat. No. 6,856,698 to Silver et al. describes a pattern matching approach that compare model boundary points with edges extracted from imagers.

The prior art demonstrates that:
(1) Computer-vision-based boundary and pattern analysis for inspection has been done since the 1970s.
(2) Prior systems have been specialize to particular inspections to be performed, using special illumination (for instance back lighting and laser illumination), and
(3) Prior systems have, for the most part, been focused on applications where high speed operation is not combined with generality or precision measurement.

SUMMARY OF THE INVENTION

This invention recognizes that advances in computer speed, imaging technology, and image processing technology now allow implementation of a truly composable vision-based inspection system. This invention further makes use of plug-in recognition modules and decision algorithms to perform the final determination on object type and quality. These advances are coupled with a modular, composable parts feeder and sorter technology enabling a high-speed system for system for identifying and inspecting ordnance, ammunition, and other objects.

The preferred embodiment includes a computer-vision system with multiple cameras for simultaneously imaging opposite sides of an object under inspection and an image processor for analyzing the imaging and determining physical characteristics of an object under investigation. The computer-vision system preferably uses one or more line-scan cameras and an image processor operative to determine an object's speed and recreate images of an object from the line data based upon the speed.

The feeder may include a bore through which an operator loads ordnance, wheels or sprockets configured to receive belt ammunition, or a bin to receive bulk ammunition in a range of sizes. In the case where the feeder is configured to receive loose objects in a range of sizes, a mechanism is included for forming a single line or column of objects for presentation to the computer-vision system. Such a mechanism may include a narrowing channel and restriction plates to form a single line or column of bullets or other objects. If the is configured to receive bulk ammunition in a range of calibers, a mechanism may further be provided for separating bullets as a function of caliber. The sorter may include a blow-off unit to divert objects found to be unacceptable, or the sorter may be manually operated.

The system architecture is 'composable' in the sense that it allows for the easy addition and replacement of different object recognition/identification modules. This increases the usefulness of the system to a variety of inspection areas. Thus, the image processor may be operative to determine the color or hue of an object, intensity, or operative to recognize alpha-numerical characters, bar codes, or radio-frequency ID tags. The image processor may further be operative to recognize imperfections associated with dents or corrosion, including corrosion due to copper sulfate leakage as might be associated with defective munitions.

DETAILED DESCRIPTION OF THE INVENTION

Figure 1:
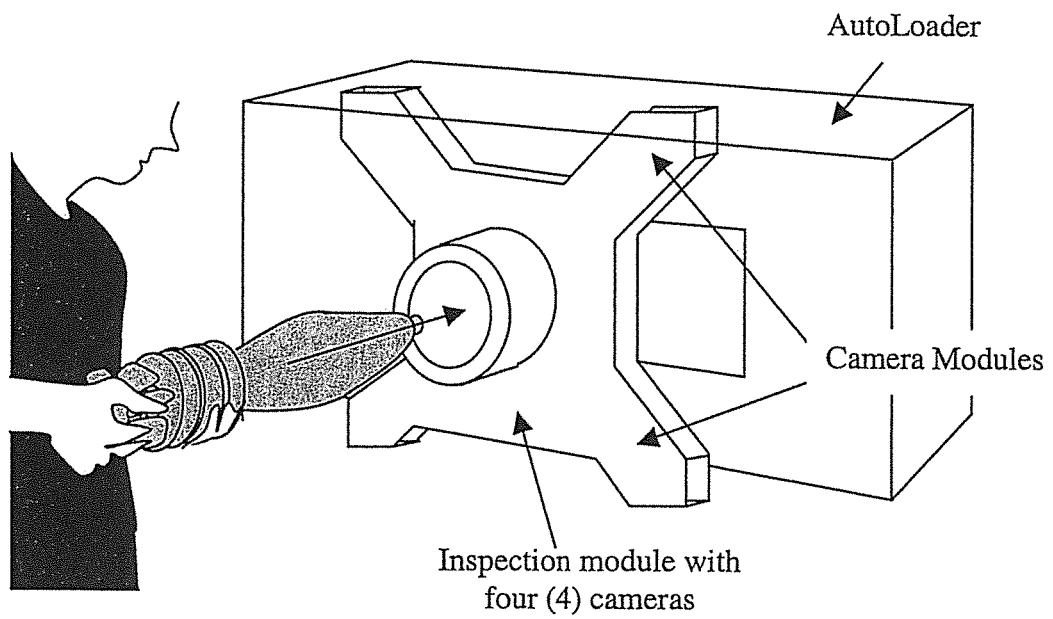
FIG. 1 is a drawing of a PIDS Manual Feed System according to the invention.

The preferred embodiment of this invention incorporates the following key components:
(1) Flexible feeder
(2) General-purpose, composable computer-vision-based inspection hardware module
(3) Flexible sorter/diverter Important aspects of the composable vision system include:
(1) Flexible, multiple-view capture imaging system/camera interfaces
(2) Plug-in vision processing modules for:
  a. Calibration
  b. Color/Hue processing & inspection
  c. Boundary finding, scaling and comparison
  d. Connected component processing & sizing
  e. Shape-from-shading and dent detection
  f. Area scanning and corrosion defect finding
  g. Text-based OCR
  h. RFID and/or Bar code processing
  i. Flexible multidimensional decision making
  j. Multiple models
  k. Automated model capture/learning
(3) GUI-based vision module composition, control and decision parameter tuning The architecture for this system is 'composable' in the sense that it allows for the easy addition and replacement of recognition modules. This increases the usefulness of the system to a variety of inspection areas. The following embodiment will be described with reference to Projectile Identification and Small Arms Ammunition Inspection. Both of these embodiments are applicable to use in ammunition manufacturing plants for in-process or end-process inspection. Other applications include machined parts inspection, recycling, entry/exit monitoring, and other uses apparent to those of skill in the relevant art(s).

Projectile Identification.

This application is used for identifying projectiles as they are loaded into the magazine of automated fire weapons. The Projectile Identification System (PIDS) provides projectile identification capability based on size, shape, color patterns, and text markings. It is hand or manually loaded and interfaces with the weapons loading system through a communication link to transfer projectile identification data. The PIDS preferably uses four (4) image sensors that can view all sides of an ordnance (with general purpose PC-based vision processing hardware) and plug-in vision software algorithms.

The PIDS utilizes 5 recognition modules and a decision module to identify 120 mm mortar shells as they are loaded into an automated weapons system. These recognition modules include a shape detection module, a hue-based color-matching module, an average intensity module, a character recognition module, and a specialized charge recognition module (for determining the number of charges on the shell). The decision module fuses the information from each of these modules to identify the type of round being loaded.

Small Arms Ammunition Inspection.

This embodiment is used for sorting and inspecting small anus ammunition in a high-speed, automated manner. The Automated Tactical Ammunition Classification and System (ATACS) can sort and inspect up to 200 rounds per minute. The first stage is a flexible ammunition feeder system for belt or bulk ammunition. The second stage is a high speed four (4) camera imaging/inspection unit that identifies round based on size, color, shape, and end markings. It is capable of determining chambering dimensions to approximately 0.002 of an inch, detecting of surface or area defects (including dents and corrosion), and determining round type. The system sorts the ammunition into individual bins based on color coding, type and quality.

The ATACS uses 5 recognition modules and a decision module to identify and inspect small caliber ammunition or similar cylindrical objects. These modules include a length determination module, a shape/damage detection module, a hue-based tip color recognition module, a gradient-based shoulder dent detection algorithm, and a hue-based corrosion detection algorithm. The decision module fuses the results from the recognition modules and determines the type of cartridge (e.g. 45 cal, 5.56 mm, 9 mm, 7.62 mm, etc.), the model number (e.g. M855, M1911, etc.), and whether or not the cartridge is defective. This system is designed to work with ammunition returning from the field. As such, the ammunition to be inspected differs greatly in appearance.

Other uses for the system include:

Machined Parts Inspection.

The technology described can be used to build small, high-speed, general purpose inspection systems for machined part identification, orientation determination, and dimensional/surface quality/color inspection. The technology was originally designed to inspect axially symmetric parts, but can be used to inspect any object if the part is presented in a known or near know orientation. Fully three-dimensional inspection is possible by including the algorithms disclosed in U.S. Pat. No. 6,173,066 to Peurach as stages in the composable inspection plug-in list.

Recycling.

The technology can be used to identify objects for recycling purposes. For example, plastic and/or glass bottles with surface markings, possible defects, and specific shapes are nearly identical to larger ordnance like those for which the PIDS system has been made. Based on their physical characteristics which include text markings, barcodes, color, shape, and size, recycle objects can automatically be sorted out of a trash stream by recyclable object type (plastics, cans, boxes, glass, etc.)

Entry/Exit Monitoring.

The technology can be used in vision systems that analyze object moving through a point of entry/exit. RFID and/or barcode tags are commonly used to identify commercial or logistical items. However, they require that the tag object be presented to the reader (in the case of barcode, to the reader view port; in the case of RFID, within range of an RF reader). In the case of active tags like RFID, the tag must be functional to operate. This technology augments these identification means with added data derived from object size, shape, color (and markings), and text. This added data can provide a redundancy check for RFID or barcode, and can provide a means for detecting packages entering or leaving through the entryway even if the RFID or barcode read fails to operate due to occlusion or malfunction. Such an entryway might be place at the loading point into or out of building or at the loading point for ISO transport containers to detecting unauthorized removal or placement of objects inside a the restricted area or ISO container.

FIG. 1 shows a manual feeder system for the Projectile Identification System (PIDS). This feeder is simply a portal through which an operator loads ordnance. As the ordnance is loaded, it passes through the composable machine vision system and is identified and inspected. Any ordnance size that fits through the portal is acceptable for manual feeding.

Figure 2:
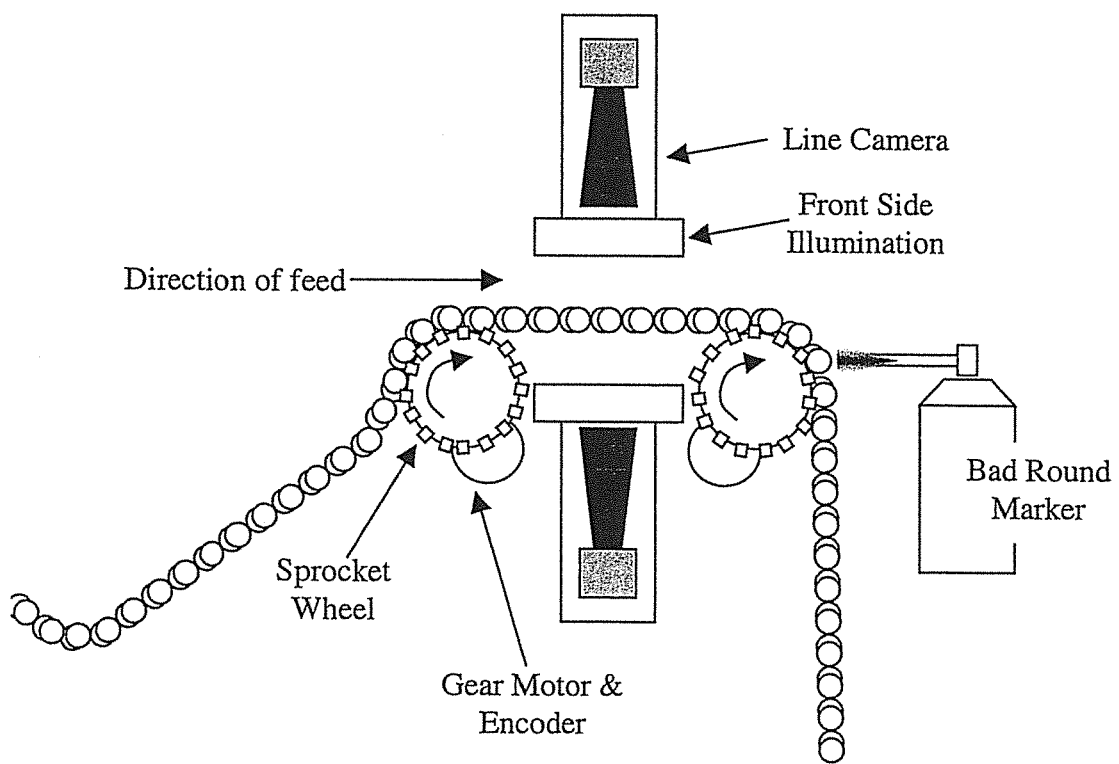
FIG. 2 shows a Sprocket Belt Fed ATACS System.

FIG. 2 shows an Automated Tactical Ammunition Classification and System (ATACS) for feeding belt ammunition. The belt is inserted into the feeder sprockets and is pulled through the composable machine vision system controlled by the gear motor assembly that drives the sprocket wheel. The position of the ammunition to be inspected under the machine vision sensors is known based on rotation measured by the encoder units attached to the sprocket (or alternatively the drive motor). Ammunition size changes are accommodated by changing the sprocket wheel sizes.

Figure 3:
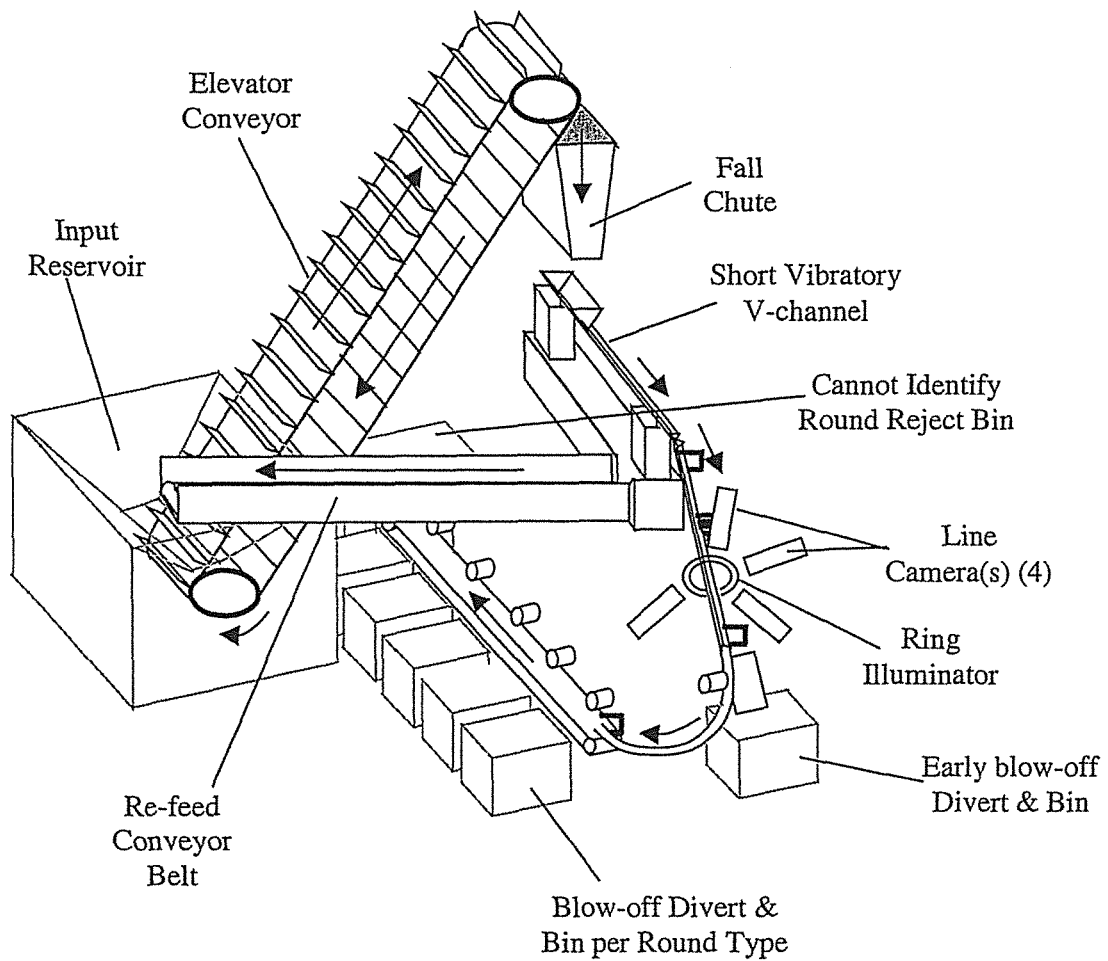
FIG. 3 is a drawing of an Automated Bulk Feed ATACS System.
Figure 4:
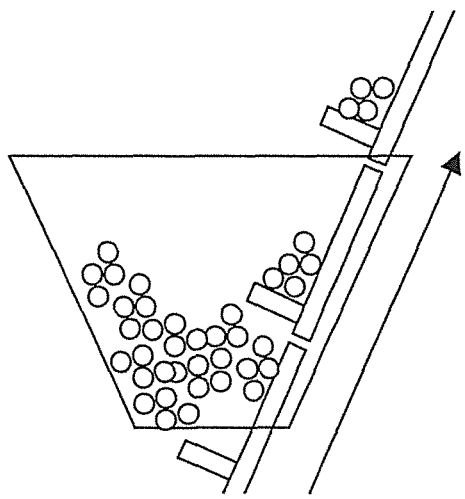
FIG. 4 depicts an Elevator Belt Scoop Ammunition from the Input Reservoir.
Figure 5A:
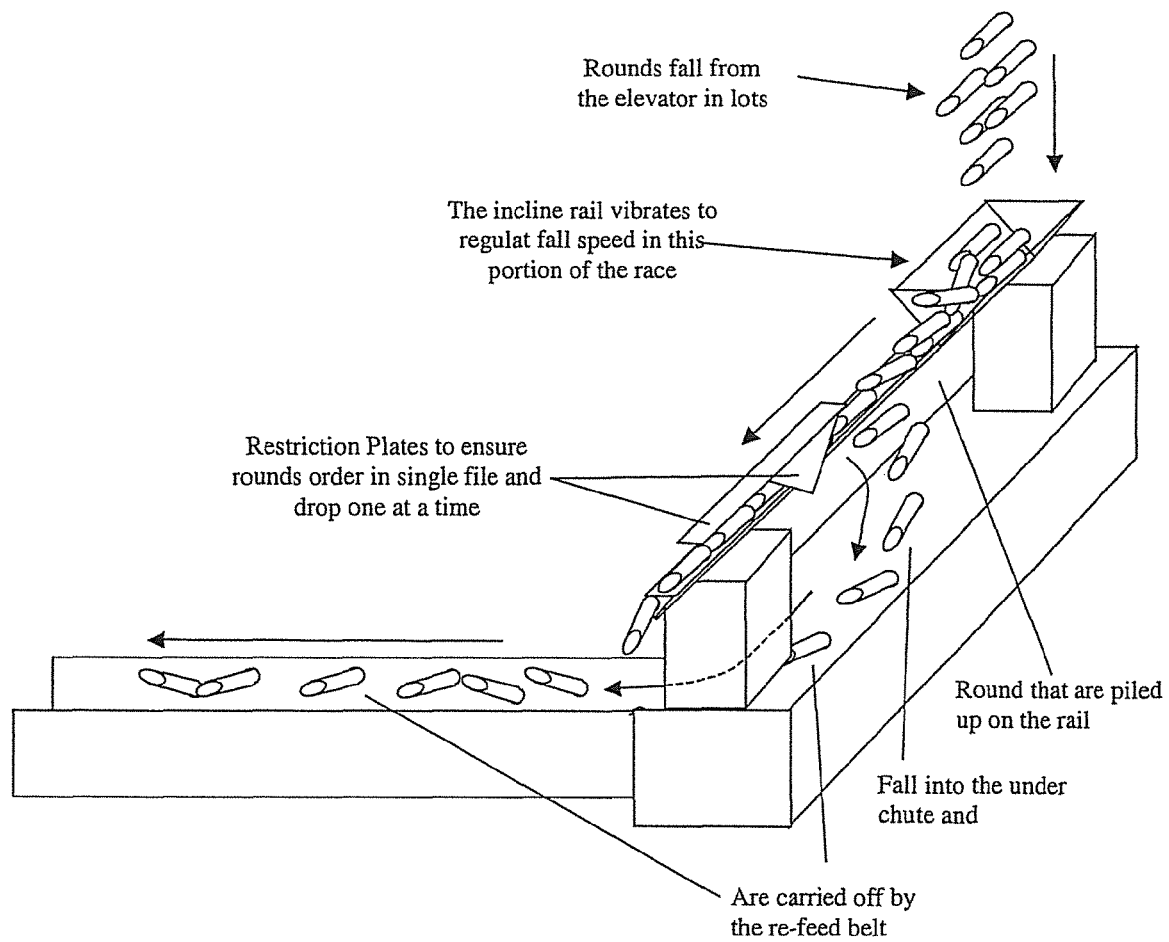
FIG. 5A illustrates a Vibratory Feeder V-Channel and Restriction Plates.
Figure 5B:
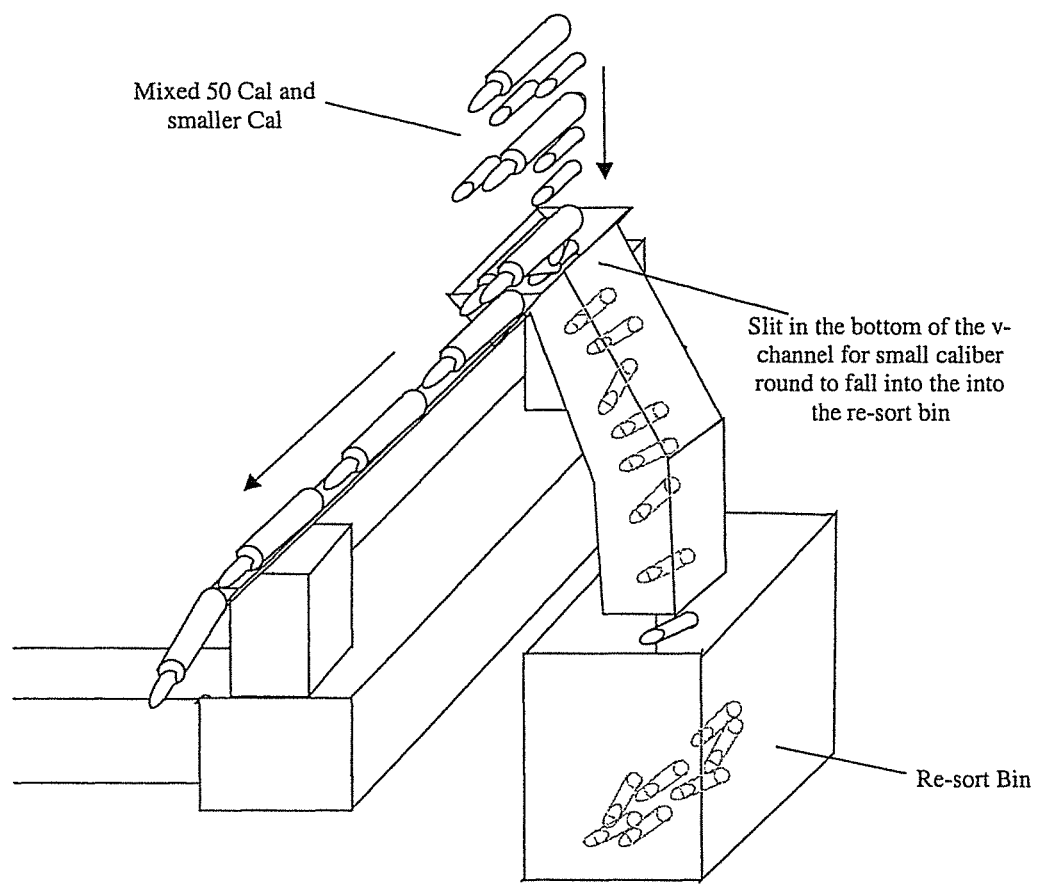
FIG. 5B shows a Vibratory Feeder V-Channel for 50 Cal separation.

FIG. 3 shows an ATACS automated feeder for feeding bulk ammunition of a range of sizes. The bulk ammunition is placed into the input reservoir. An elevator conveyor moves through the input reservoir at a steep angle and the protruding portions on the belt scoop up a lot of ammunition (without specific selection of any particular type or size—FIG. 4). The elevator moves the lot of ammunition up and over the end, dropping it into a fall chute that ends in a short v-channel (FIG. 5). The ammunition that is caught by the v-channel moves down a slight incline, speed regulated by regular adjustable vibrations of this channel.

The channel narrows and has restriction plates attached so that only a single line or column of bullets can move down the line to the point of entry into the composable machine vision inspection stage. Rounds that do not singulate into a single file fall into a conveyor belt that takes them back to the input reservoir for re-feeding. Trial and error have shown the inventors that the particular shape and number of the restriction plates shown in FIG. 5 are necessary to prevent feeding multiple bullets into the inspection stage at or nearly at the same time. Because 50 Cal and smaller rounds feed substantially differently, a v-channel has been designed which sorts 50 Cal separately from smaller caliber. For the arrangement shown in FIG. 6, the 50 Cal move down the channel for inspection and the smaller caliber rounds fall through a slit in the bottom of the v-channel into a re-sort bin.

The machine vision system can use any of a variety of means for forming images of the objects to be inspected. Single CCD cameras for imaging one side of an object from a single view point is the lowest cost and easiest approach. However, the systems shown in FIGS. 1-3 image objects on all sides simultaneously so that full surface inspection is possible. Use of area cameras is possible for some lower resolution applications, however, the systems shown in the figures, used higher resolution line cameras (2000 color pixels or greater) for precision measurement. To form an image, therefore, it is necessary to move the object through an active imaging area at a known rate of progression so that the two dimensional image can be reassembled from multiple line images.

Figure 6:
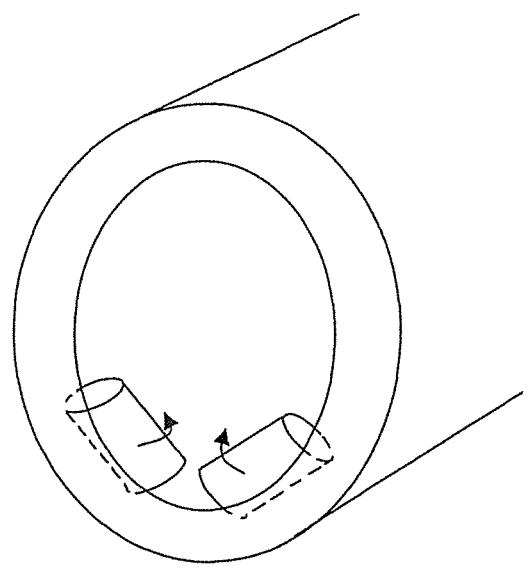
FIG. 6 is a drawing of a Guide roller.

For the system in FIG. 1, this is accomplished by measuring the revolution of a guide roller upon which the ordnance under inspection moves as it is inserted through the inspection mode (FIG. 6). For the system in FIG. 2, measuring the rotation of the feed sprockets controls the ammunition feed rate. This provides the measurements needed to assemble ammunition images in this case. In FIG. 3 the drop length, velocity, and acceleration of an ammunition piece are measure by four LED or laser detector devices.

Figure 7:
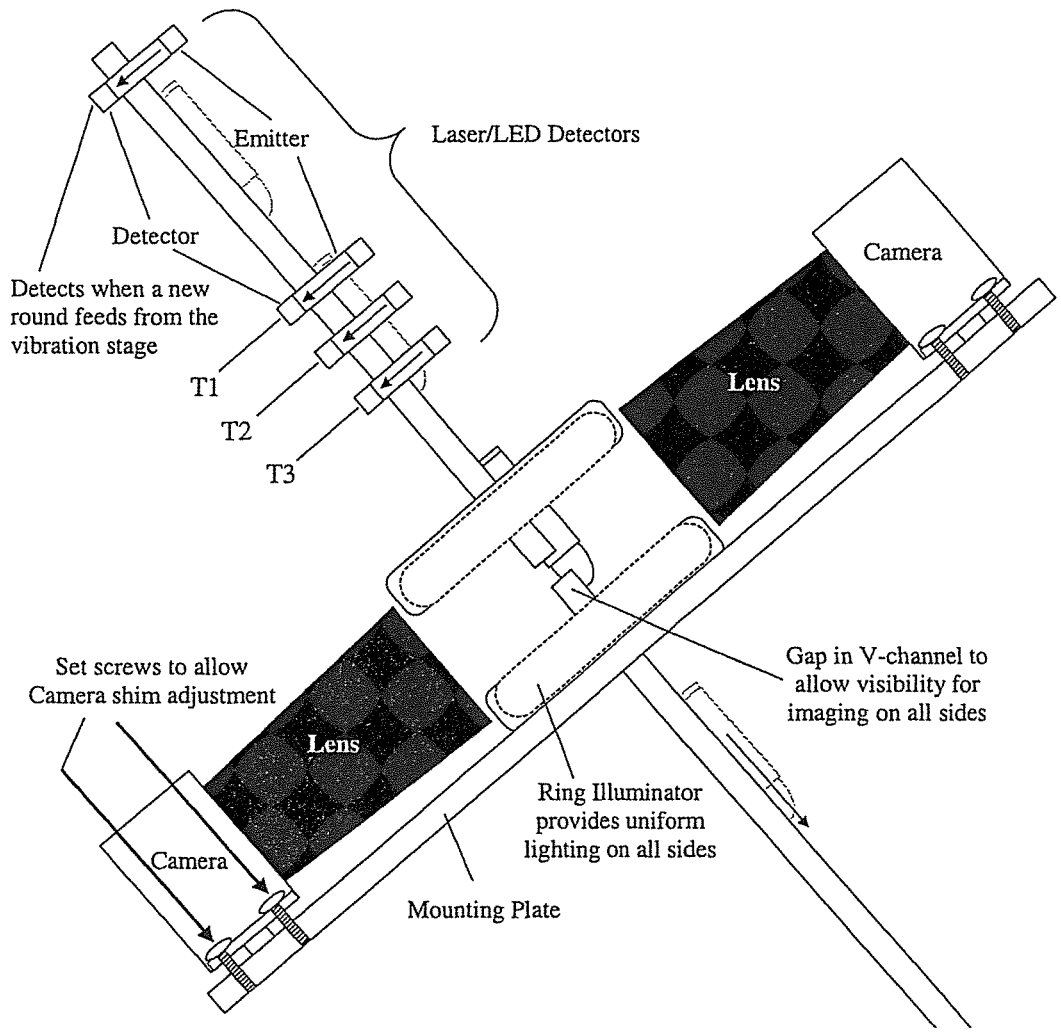
FIG. 7 depicts a V-channel and sensors in the identification and inspection module.

Referring to FIG. 7, the bullet moves off of the vibrating incline v-channel and passes through the first LED or laser detector. This detection informs the controller that a bullet is in the inspection inclined v-channel and can control the vibration stage to control the bullet feed rate. This v-channel is a hardened slippery material with good wear characteristics so that the bullet moves smoothly down and accelerates at a predictable rate, which is a fraction of the acceleration due to gravity. The bullet then passes through the three detectors located close to the imaging sensor point. These three measurements provide the data needed to precisely measure the rounds length, speed upon exiting past the last detector and the round's acceleration. Time taken for the bullet to fall by each of the detectors provides an estimate of bullet length (assuming an estimate of the velocity and acceleration). Time take for the leading or trailing edge of the bullet to fall from point T1 to T2 or point T2 to T3 provides an estimate of the velocity of the bullet assuming (assuming that the acceleration is known). And the difference in time between leading/trailing edge falling from T1 to T2 compared to T2 to T3 provides and estimate of acceleration. These parameters are assumed to be approximately correct (with speed adjusted based on measured acceleration) as the round drops through the image capture point.

Figure 8:
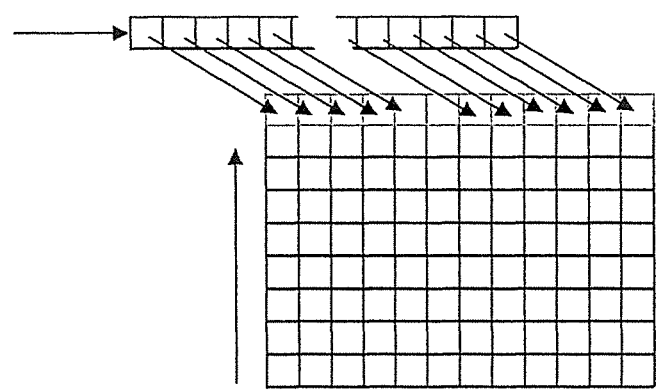
FIG. 8 illustrates an Image assembly.

The line scan imaging sensors capture an image line-by-line for all three feeder approaches which are assembled into multiple color 2D images comparable to those from conventional area scan cameras of high resolution (FIG. 8).

Figure 9:
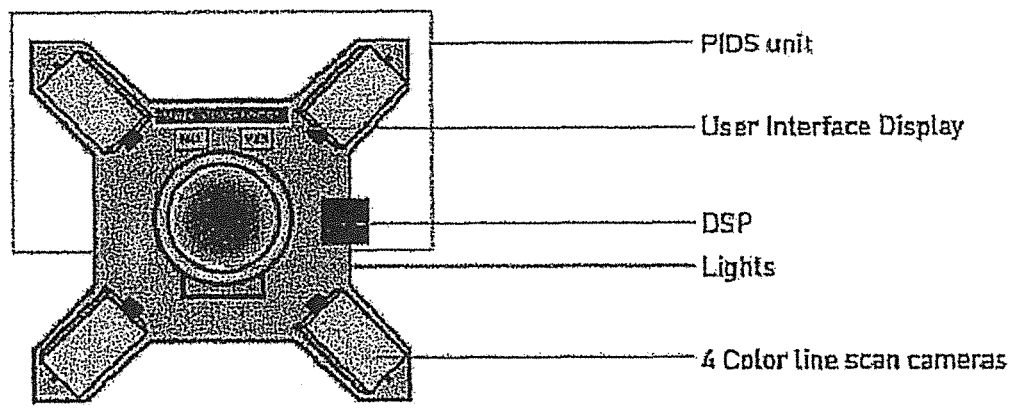
FIG. 9 shows a PIDS camera arrangement.

In the embodiments shown in FIG. 9, four (4) cameras are used to achieve the desired aerial coverage and resolution, however, more or fewer cameras could be included at the imaging stage. In all of the systems, uniform ring illumination is used so that all cameras can be active at the same time. However, in some systems (for instance FIG. 2) fewer cameras might be used with backlighting or front lighting to enhance the object features that are to be measured (ring illumination emphasizes all areas, front side illumination emphasizes object edges and front facing surfaces and surface texture, and backlighting emphasizes edges or silhouettes only).

Figure 10:
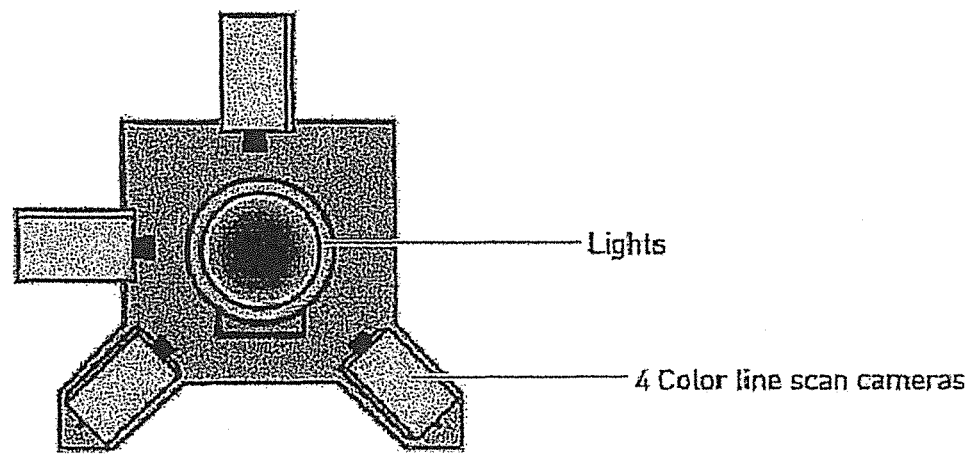
FIG. 10 is a drawing of an ATACS camera arrangement.

FIG. 10 shows a variation of the camera arrangement of FIG. 8 that is used for the ATACS ammunition inspection system. The PIDS inspection system arrangement shown in FIG. 8 provides for uniform aerial coverage so that color, shape, and text can be read equally well on all sides of the ordnance. The non-uniform arrangement for the ATACS inspection system shown in FIG. 10 provides for uniform spacing of bullet profile or edge data sections (eight equally spaced profiles around each bullet), at the expense of a non-uniform aerial coverage. This is an acceptable trade-off because there is no text marking on small arms munitions and surface changes due to corrosion tend to be spread over large areas of the bullet if they are present and will not be missed in spite of nonuniform aerial resolution.

Figure 11:
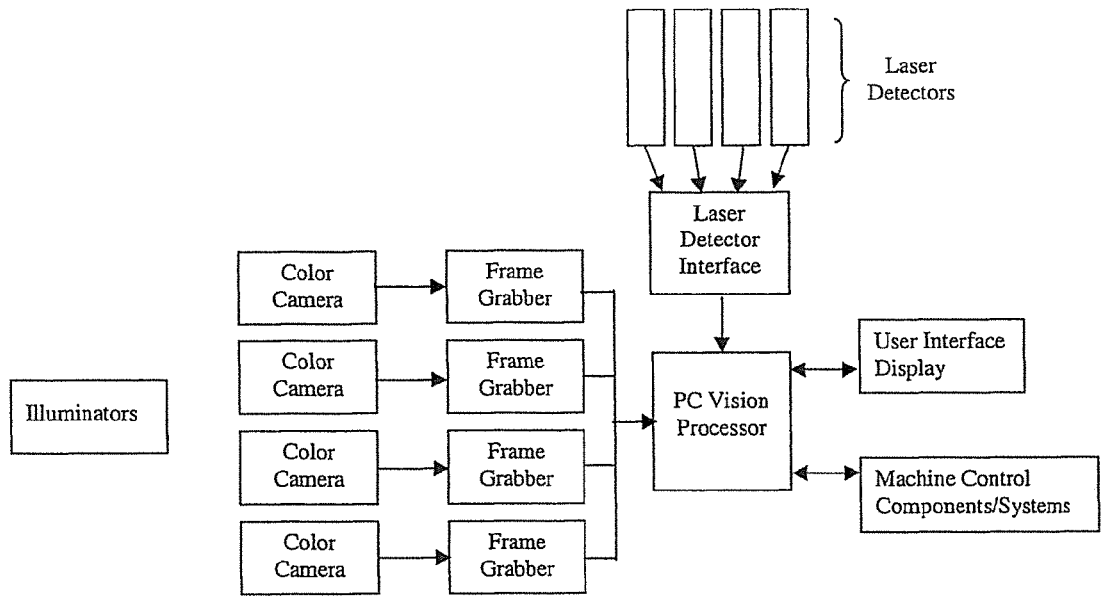
FIG. 11 depicts a Composable Machine Vision System Block Diagram.

The hardware arrangement supporting the preferred four (4) camera system is shown in FIG. 11. The system uses four (4) high resolution, high frame rate, color Atmel AviivA C2 CL 4010 line scan cameras, 4 Matrox Meteor II CameraLink frame grabbers, a standard PC, a set of illuminators, a user interface display, and a communication interface to machine control components that sort or divert based on inspection outcome. The key to this sensor module is the use of high resolution, line scan cameras. This enables the recognition hardware to be packaged in a small, portable form. Alternative object inspection systems use either standard or high frame-rate area cameras.

The line scan hardware has two major advantages over the use of the more traditional area cameras. First, the line scan hardware allows for a much smaller inspection area, while still inspecting the entire object. For example, when inspecting 120 mm mortar shells, a traditional area scan camera needs to view the entire length of the round at one time (roughly 2 feet). However, the inspection area for the line scan system is only a few millimeters. For applications where the object is already moving (or can be made to move) the line scan hardware enables the creation of a much smaller sensor module. Second, the images collected by the line scan hardware do not blur when the object is in motion. For an alternative area camera system, the image acquisition must be synchronized with a strobe light to remove unintended blur from the images of fast moving objects.

Upon completion of the identification and inspection process executed by the composable machine vision module, each round is classified by type and by good/bad. If a round is bad it is sorted into a reject bin. Otherwise the round is sorted into a good bin and the bin count is incremented. For the PIDS system, rounds are inserted into the designated autoloader slot, and the contents of the slot are communicated to the autoloader controller (FIG. 1—autoloader is behind the PIDS sensor).

For the belt fed ammunition ATACS system, bad rounds need to be de-linked and replaced. This is a complex mechanical operation and is usually performed by manual means. Therefore the belt ATACS system simply marks the bad round with paint for later manual intervention (FIG. 2—marker is shown there).

Figure 12:
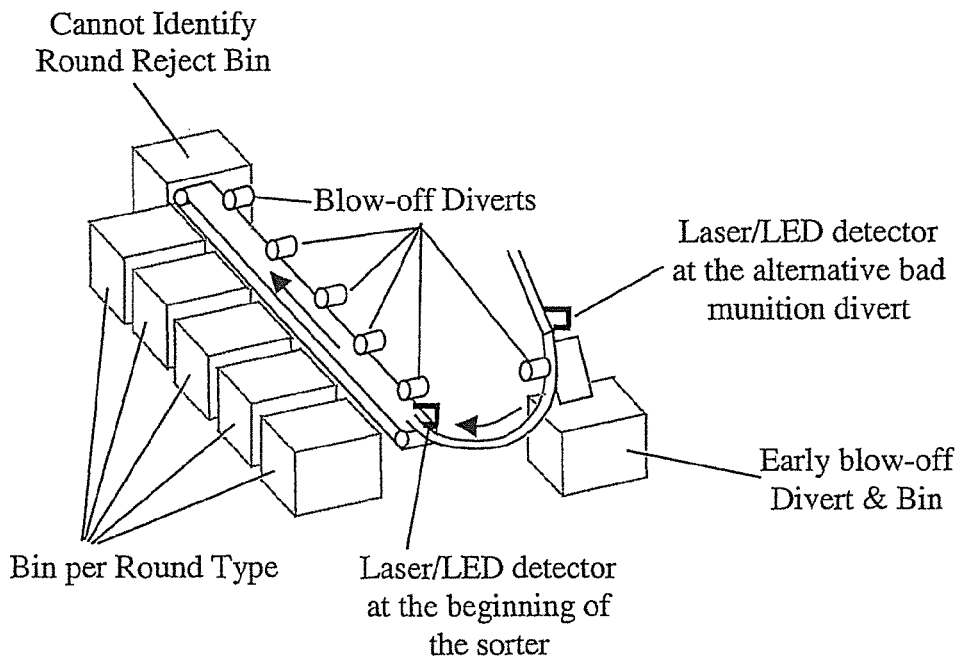
FIG. 12 illustrates an ATACS bulk ammunition sorter/diverter.

For the bulk feed ATACS system, rounds are dropped through a circular ramp to a belt feed-based sorter unit (FIG. 12). Each round passes through a laser/LED detector at the beginning of the sorter to mark when the round is presented at the beginning of the sorter belt. Sort bins are located at uniform positions along the belt opposite from computer controlled blow-off air jets. Because the belt is controlled to a uniform speed, a round can be sorted to a particular bin by actuating the opposing blow-off jet timed from when a round is marked at the input laser/LED detector station.

The sorter controller accepts the bin assignment information from the composable machine inspection module as the round is falling towards the sorter unit. When the round is detected and marked at the input LED/laser detector station, a timed task is initiated that will track the bullet until it is in position for the blow-off event into the assigned bin. The air jet is actuated for a short pulse period and compressed air blows the bullet into its assigned bin. The logic of the sorter allows for multiple bullets and blow-off events occurring simultaneously to maintain a high sorter throughput rate. Diverter approaches like that described in Linton (U.S. Pat. No. 6,822,181) could be alternatively be employed in the sorter.

Two additional bins, one at the end of the belt and one before the bullet has passed through the input laser/LED detector station, is included in the sorter (also shown in FIG. 12). The first bin is an alternative bad munition divert station. The air jet blow-off for this bin can be actuated at a timed interval after bullet is detect at the divert LED/laser sensor. The bin located at the end of the sorter belt is used for bullets that fail to be identified by the inspection module—this is generally a low probability event but can occur due to a variety of inspection algorithm failures that prevent the system from properly classifying a particular round as any known type.

Figure 13:
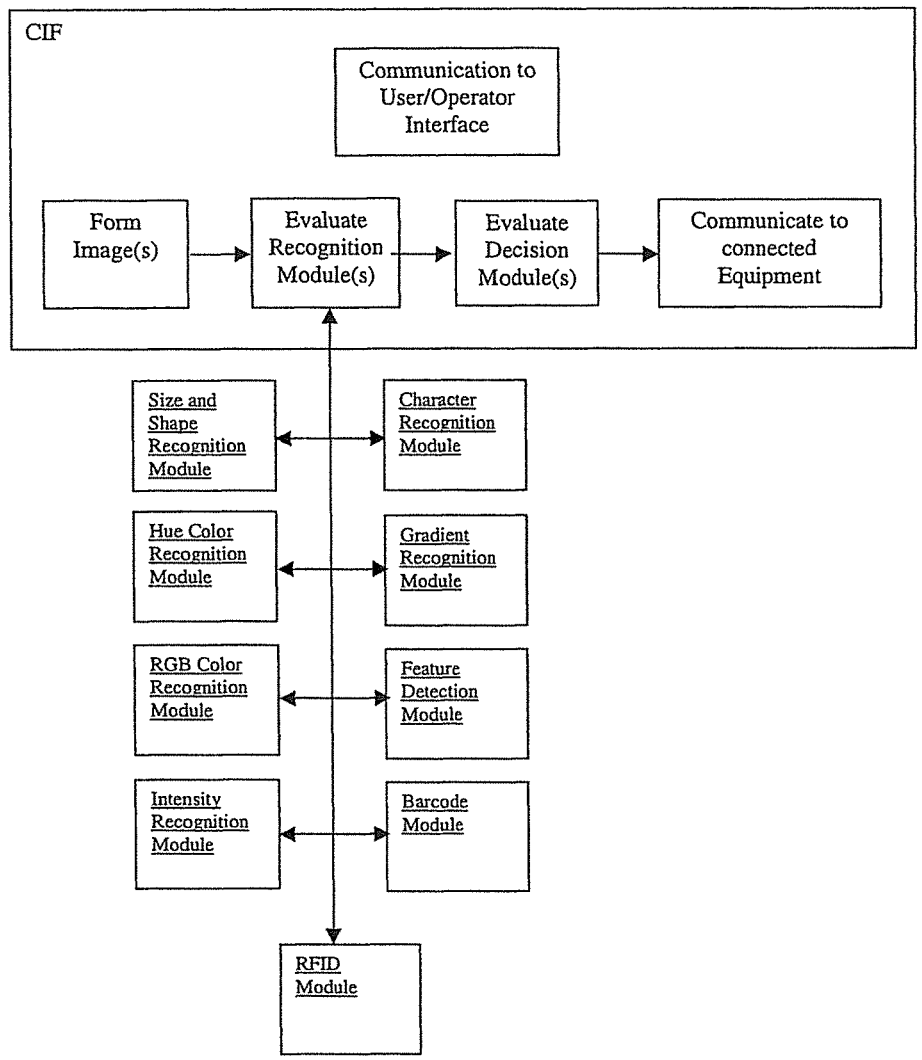
FIG. 13 shows a Composable Identification Framework Block Diagram.

The composable machine vision module is based on a Composable Identification Framework (CIF). The CIF coordinates and controls all of the plug-in software modules (see FIG. 13). This includes the image capture hardware driver modules, the recognition modules, the decision module, and any user interface modules. The CIF also manages the communication between the inspection system and the sorter equipment that relies on its object classification/inspection results (such as the weapon systems mission control system for the PIDS or the bad round marking device or sorter/diverter for the ATACS).

The CIF monitors the data captured by the inspection hardware to determine when an object passes by the line scan cameras. This detection occurs through a simple background separation algorithm. Once the presence of an object is detected, the system assembles four (4) images of the object from the line scan data. The CIF collects data from object motion detection sensors to determine the speed of the object for each line in the image. This information is used to properly construct, correct, and subwindow the image for use by the recognition modules.

The CIF then sends these images to the recognition modules to score the new object against a set of metrics (this can include size, shape, color, intensity, character recognition, corrosion, physical features, RFID, barcode, etc.). The CIF is designed to allow the flexible addition (composition) of new recognition modules. The results from the recognition modules are sent to the decision module(s) that is(are) responsible for determining the identity and quality of the detected object through fusion of the results from the multiple recognition modules. The CIF sends the result of the decision module to the user interface or other connected equipment to control sort/divert or other after inspection operations.

The CIF system is designed in a modular fashion so that recognition modules can be added to or removed from the system. The main purpose for this is to allow for easy expansion or reconfiguration of the recognition system. This capability is exploited to quickly create new inspection systems from the present embodiment.

The identification and inspection system is composed of individual recognition modules that can be used to aid in the process or object identification and inspection. Existing modules include the following:

Size and Shape Recognition Module:

The shape recognition module is capable determining the 2D profile of the object presented in an image subwindowed to include the complete object to be inspected. The profile information is collected through an edge detection process that is optimized to yield accurate subpixel position boundary information under the optical and uniform illumination conditions present in the PIDS or ATACS imaging system. The system is designed to be used in environments where it is difficult to keep the optics clean (industrial applications, military uses in the desert, etc.) Therefore, the edge detection algorithm was designed to negate the effects of dust and light dirt on the optics.

Figure 14:
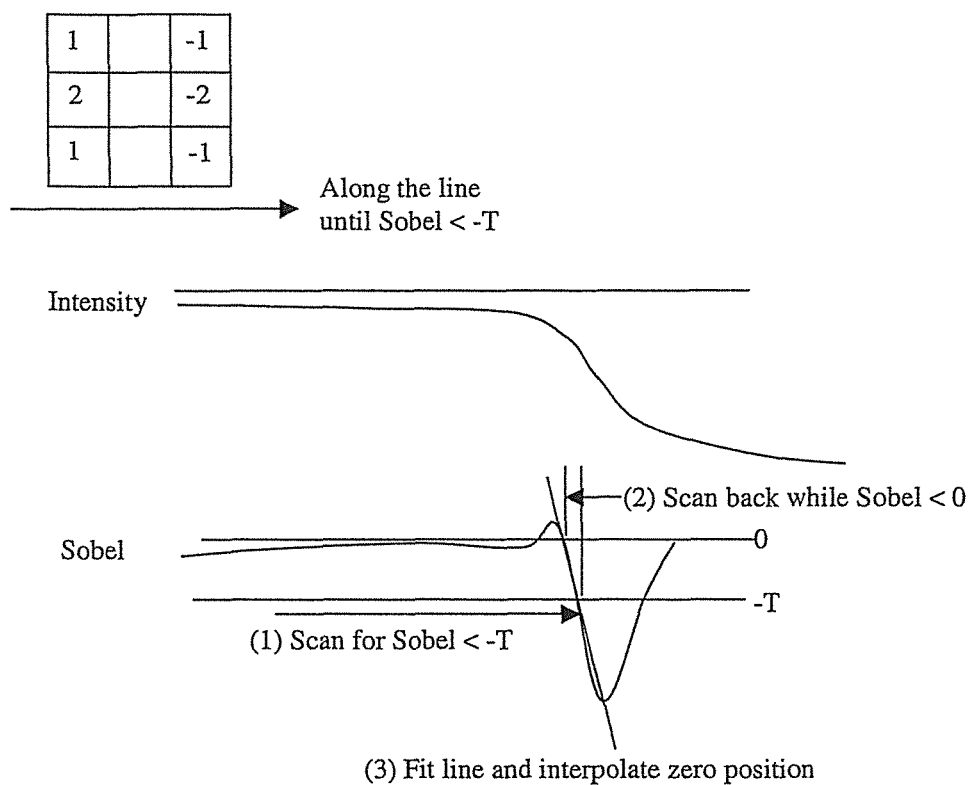
FIG. 14 depicts Sobel Operator Edge Detection.

The edge locations are determined in the following way scanning from the subwindow boundary left to right (to get the left edge) and also from right to left) to get the right edge):
(1) form the Sobel operator (FIG. 14).
(2) if the magnitude of the Sobel is <−T then an edge has been identified other move over one pixel and repeat (1).
(3) Back up and reevaluate the Sobel operator.
(4) If the magnitude of the Sobel is <0 repeat (3)
(5) Use the Sobel magnitude at this position and the Sobel magnitude at the previous position as two points along a line. Perform linear interpolation to determine the subpixel position where the Sobel magnitude would =0. This is the best edge position.

This relatively complex boundary detection algorithm is required to overcome rather substantial boundary position errors generated by simpler edge location approaches generate due to substantial inspection object surface reflectance related variation (from very shiny to very mat).

The shape recognition module matches the collected edge information against stored template data for known objects. If they match within a selectable tolerance, $\Delta_{identify}$, then the object has the same shape as the template object. In most cases, this information alone is not enough to predict the identity of the object. Therefore, the information is sent to the decision module to be used as part of the decision making process.

The shape recognition module can also be used to detect damage on an object. Damage is detectable through smaller differences, $\Delta_{inspect}$, between the template and the collected edges. These differences can be mapped to an actual defect size based on properly calibrated optics of the imaging hardware. Generally:

$$\Delta_{identify} > \Delta_{inspect}.$$

Finally, the shape recognition module creates boundaries for the other recognition modules. The other modules only need to analyze data within specific areas of the identified object. The shape recognition module stores the edge map for the object. The other modules will only analyze data within the object, as delineated by the edge map.

The shape recognition module creates an overall object size (length, width, etc.) by determining the bounding box of the edge maps.

Figure 15:
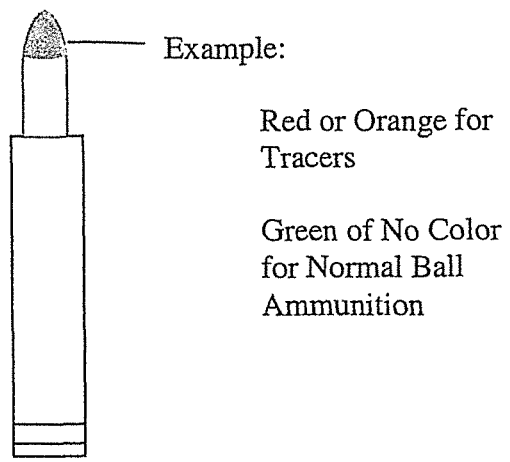
FIG. 15 is a drawing of a Color Coding on Bullet Tip.
Figure 16:
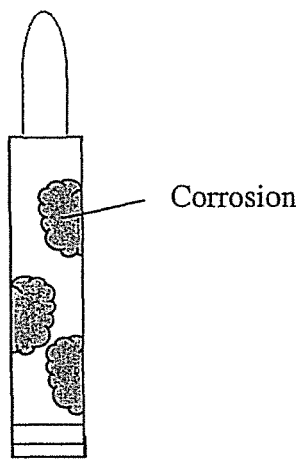
FIG. 16 depicts a Color-based Corrosion.

Hue Color Recognition:

The hue color recognition module detects hue color information. This module detects hue color information in bands, blobs, or average for the entire object. This information is used to further identify the object type or to find defects. For example, hue color is used to identify the model type for ammunition within a caliber (FIG. 15—M855 has a green tip, M856 has an orange tip, etc.). Hue color is used to find corrosion on an object—Copper Sulfate related corrosion due to propellant leakage causes corrosion spots with a green band tint—FIG. 16. The results of this module are sent to the decision module for final decision on the object type and quality.

RGB Color Recognition:

The RGB color recognition module detects RGB color information. This module detects RGB color information in bands, blobs, or average for the entire object. This information is used to further identify the object type or to find defects as an alternative color model to Hue and Saturation (the Hue Color Recognition module).

Figure 17:
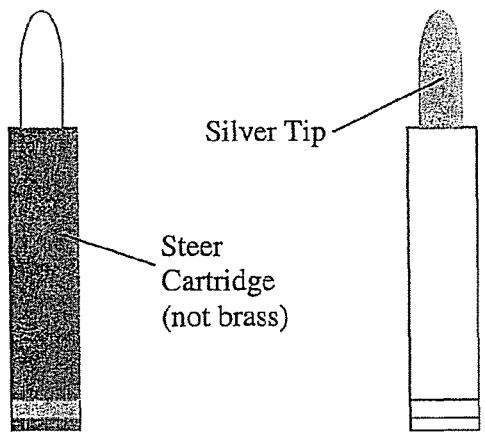
FIG. 17 illustrates a Nonstandard casing or bullet materials.

Intensity Recognition:

The intensity recognition module detects intensity information in blobs, bands, or average for the object. Intensity information can be used to determine the material type of the object. For example, this module is used to determine if an ammunition cartridge is steel (gray) or brass or the bullet tip is silver or copper (FIG. 17). The intensity information is used to determine if an object is painted a dark color or a light shade. Since the color recognition modules attempt to determine color separately from intensity, intensity information is necessary to differentiate different shades of a particular color.

Figure 18:
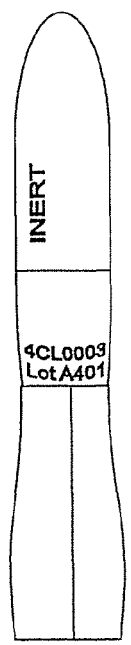
FIG. 18 shows Text Markings.

Character Recognition:

The character recognition module includes a gradient-based algorithm for finding the location of text on an object. Then it employs optical character recognition to identify the characters in the identified region (FIG. 18). This module is useful for reading information such as model numbers and lot numbers that may be included on an object.

Figure 19:
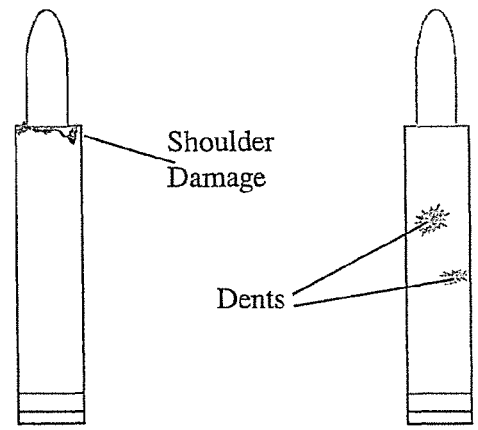
FIG. 19 is a drawing that depicts Shoulder and dent gradients.

Gradient Recognition:

The gradient recognition module examines the image and detects pixel gradients that are associated with specific types of dents. The system can be set to flag the gradients based on gradient magnitude or direction. This module has been used to detect dents on the shoulder area of small arms ammunition—FIG. 19.

Feature Detection:

The system includes the ability for compound feature detection. Typically, the exact feature detection composition depends on what is to be detected. For example, we have implemented an algorithm for determining the number of charges on a 120 mm mortar shell by counting the number of "charge" features present.

Barcode:

The system accommodates a standard barcode reading mechanism for incorporating commercially defined bar code readers.

RFID:

The system accommodates a standard RFID reading mechanism for incorporating commercially defined RFID code readers.

The system can be expanded to include new recognition modules coded as software plug-in modules. These can include modules such as, eddy current analysis, ultrasound analysis, laser spectroscopy or interferometry, etc.

The decision module is responsible for compiling the results from all of the recognition modules to determine the identity and quality of the object.

The Sensor Module bundles all of the software modules needed to drive the image capture hardware devices and associated sensors.

Figure 20:
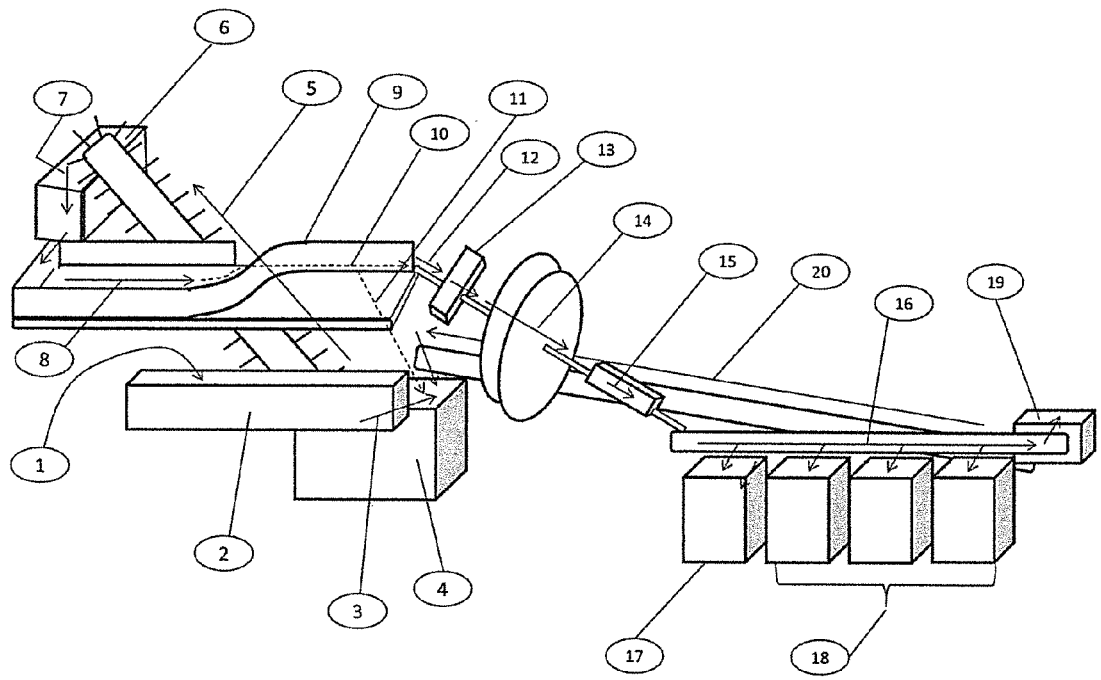
FIG. 20 illustrates various Inspection Machine improvements.
Figure 21:
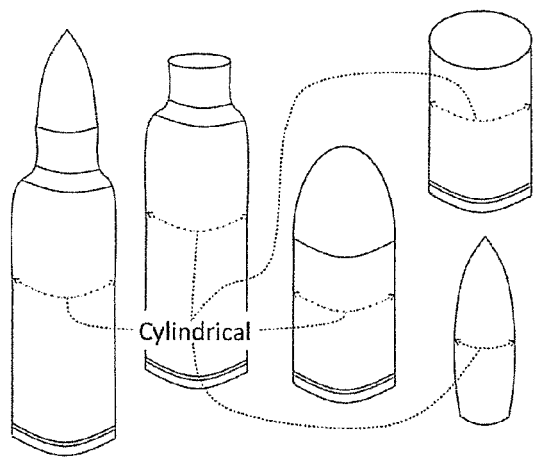
FIG. 21 shows representative cylindrical part types inspected.

FIG. 20 is a drawing that schematically illustrates an inspection machines constructed in accordance with the invention including certain improvements and modifications. In particular, this embodiment may be configured for inspection of other ammunition related parts including balls or bullets, blanks, and spent or empty cartridge cases as shown in FIG. 21. In FIG. 20, the numerically labeled items as defined as follows: (1) is where bulk and dirty rounds are inserted; (2) is an input tray for bulk and dirty ammunition in which the dirty rounds can be manipulated over a screen table to remove dry dirt and mud before moving the batch into the inspection machine; (3) is a transfer gate through which cleaned rounds can be pushed into (4) the input hopper. (5) is an elevator conveyor that lifts "handfuls" of rounds up and dumps (7) into a vibratory hopper (6).

The vibratory hopper dumps into a flat conveyor shown moving left to right in FIG. 20, item (8). As the conveyor moves, the area that can support rounds necks down as shown in (9). This leaves room for only single file lines of rounds (10), with any others falling back down into input hopper for recycling (11). The single file line remaining is dropped onto the v-channel (12) and falls through the v-channel incline through a series of inspection heads (three shown are (13) the sealant inspection head, (14) the side imaging and profileometers, (15) the head-end and tip imaging and inspection).

After inspection is completed, the v-channel deposits the rounds onto the sorter conveyor (16). Depending on how the inspection system classified a round, it is diverted into one of the bins (17) & (18)—typically bad rounds go in (17) and good rounds of different types are diverted into the one of the bins (18). If a round could not be correctly classified it goes to the end of the sorter conveyor (16) and is diverted (19) into the return conveyor (20) for recycling back to the input hopper (4).

Figure 22:
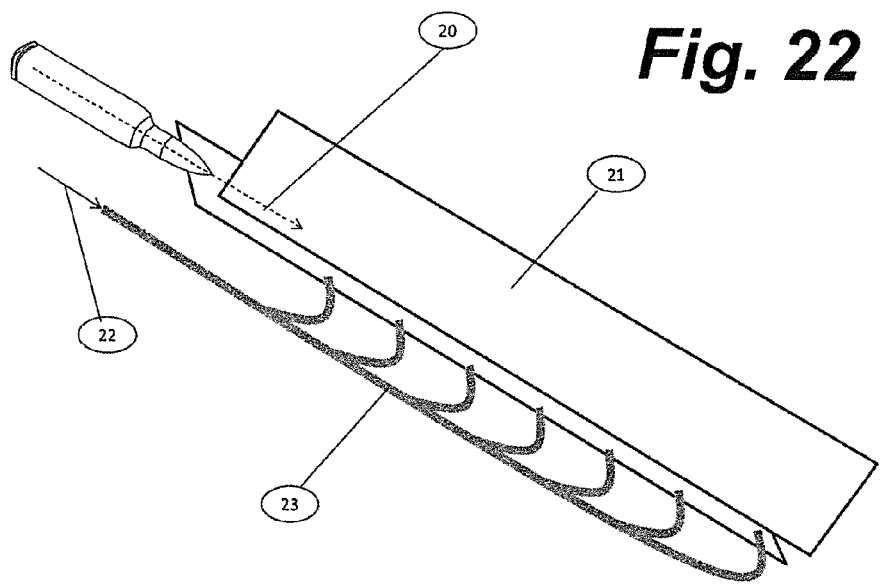
FIG. 22 depicts the use of air pressure to reduce friction.
Figure 23:
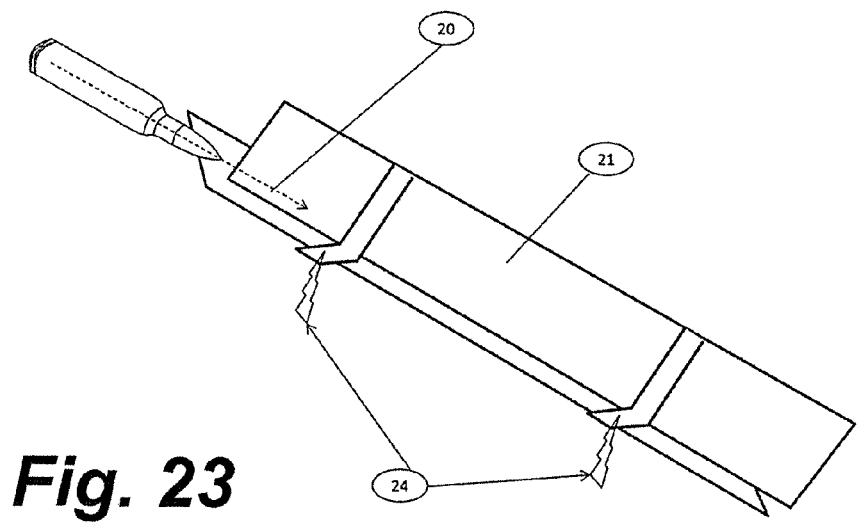
FIG. 23 depicts the use of vibration to reduce friction.
Figure 24:
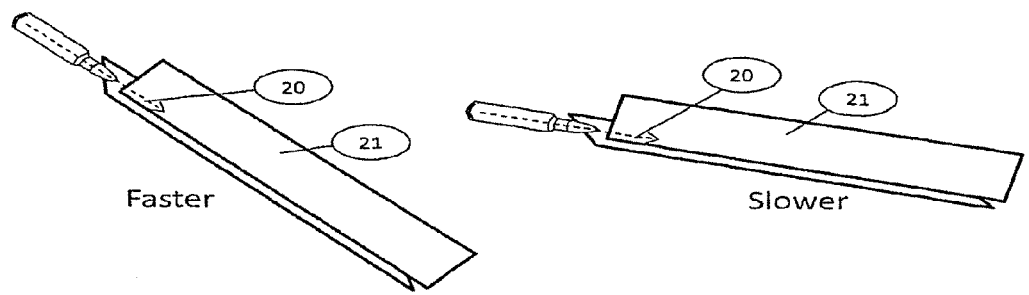
FIG. 24 shows different angles of decent to reduce or increase speed.
Figure 25:
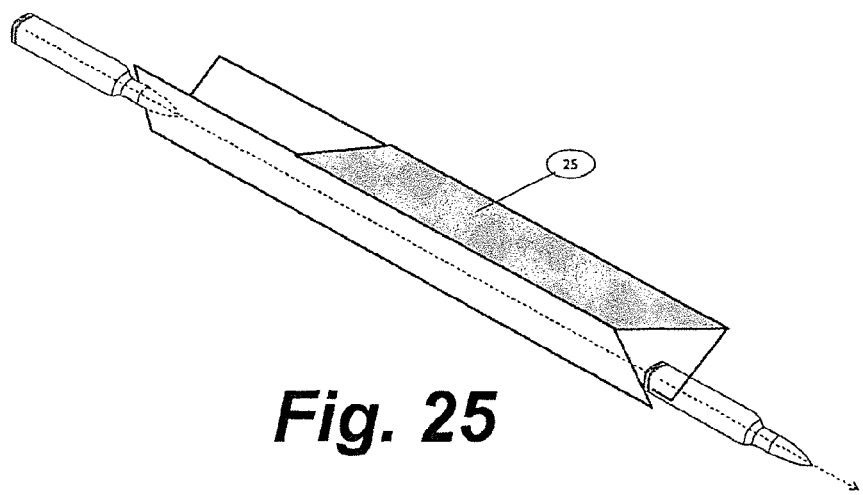
FIG. 25 illustrates channels that restrain part motion out of a channel during path change maneuvers.
Figure 26:
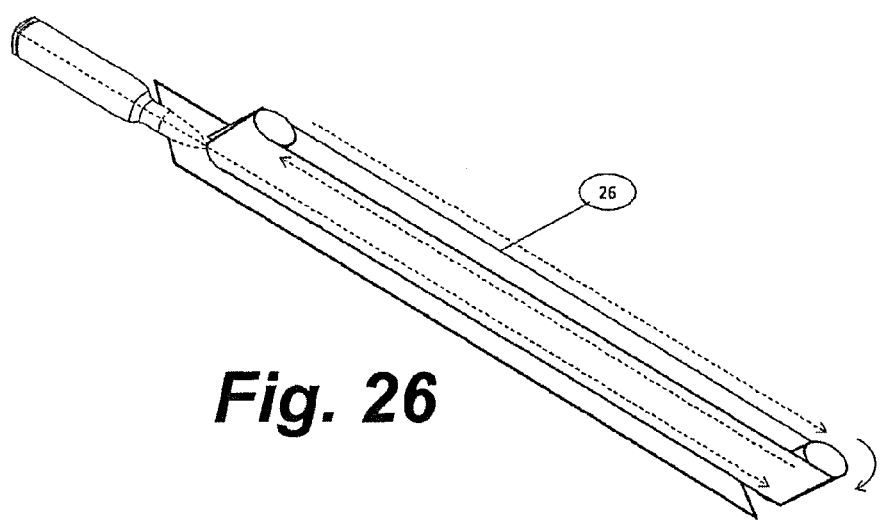
FIG. 26 shows a belt v-channel.

The basic method of inspection, singulating the items into a single file stream of part passing through an imaging and profiling inspection head remains the same, as do all of the side and profile inspection methods that are able to be or are optionally performed:

a) Eddy current for defect detection
b) Ultrasound analysis for defect detection
c) Laser spectroscopy for defect detection d) Laser interferometry for defect detection
e) Barcode reading for model number and lot identification
f) RFID reading for model number and lot identification
g) Size profiling for type identification and defect detection
h) Shape analysis for type identification and defect detection
i) Hue or RBG color analysis for model type, material type, or corrosion detection
j) Intensity analysis for material analysis and defect detection
k) Gradient feature detection for dents and other defect detection,
l) Shape from shading to detect 3D structure from intensity and gradients,
m) Strobe light gated camera,
n) Laser illuminated camera, or
o) Character recognition for number and lot identification Additional apparatus have been developed for regulating part speed down (20) the v-channel rail (21). These mechanisms include:
a) Pressurized air jets (22) and (23) to reduce channel friction (make the part type move faster)—FIG. 22
b) Vibration (24) also can make the part move faster—FIG. 23
c) Different rail material (makes the part move faster or slower)
d) Different angles of decent (make the part move faster or slower)—FIG. 24
e) Replacing the v-channel with sections of tube or boxes with tops or "roofs" (25) reduces part motion variations during part path changes—FIG. 25
f) Replacing the v-channel with conveyors to (26) more carefully control part motion speeds—FIG. 26

Figure 27:
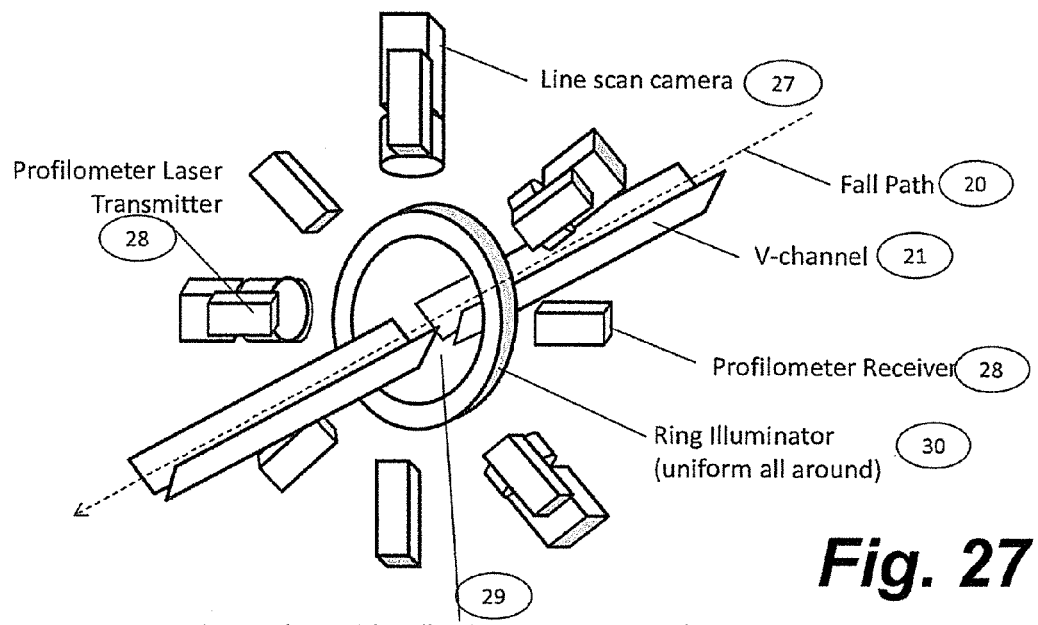
FIG. 27 depicts profile and all-sides inspection.
Figure 28:
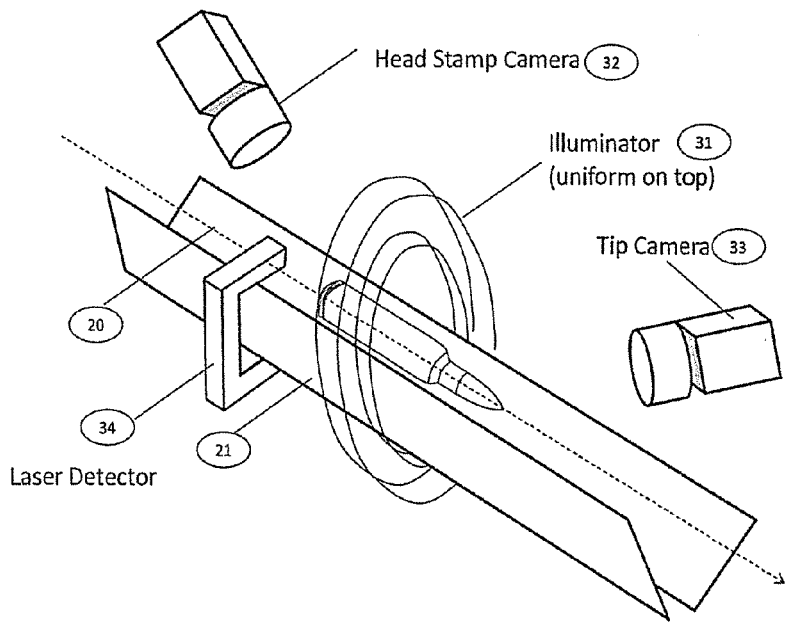
FIG. 28 shows tip and head stamp cameras and an illuminator.

In addition, core side image (27) and profile sensors (28) image through gaps (29) in the v-channel (21) and their illumination (30), shown in FIG. 9, additional inspection stations have been added to detect:
Head stamps—character marking on the back of a round that indicate model number or lot number. FIG. 28 shows the sensor arrangement for head stamp and tip inspection.
Primer position (33)—image recognition system for identifying that a prime is flipped around, is in too far, is not in far enough, is misaligned, or is missing altogether.
Tip or mouth opening position and shape—mouth out of round or the tip not positioning in the center of the mount opening indicates a defective part (detected in the imagery for tip (33) and head (32)).
Higher discrimination of color to detect nickel vs. brass cases (detected in the all-side cameras (28) in FIG. 27)
Assurance to US Army standards that spend cases can be reliably separated from case still with balls into them (i.e. probably not shot).
Modification of case visual inspection algorithms to operate on polymer cases as well as metal one (steel, nickel or brass).

FIG. 28 shows two tip (33) and head stamp cameras (32) and their illuminator (31). These cameras image the round from an angle above the v-channel rail path (21) with a uniform illumination (not strobed) to capture the front of the round and the back of the round (front can be the mouth or the tip; back can also be called the head and markings on the head called the head stamp). To capture the moving cartridge head (32) and tip (33), two area cameras with integrate time control are manipulated to stop the motion. The front and back images are capture as a round passes through the inspection station triggered by a laser detector (34) positioned just before the inspection station.

Because the system processes mix ammunition, based on part identification that occurs before this station the time between the trigger and the imaging process is adjusted by round speed and size. Because our system supports feeding rounds in front to back order or back to front order, the image processing system determines if the up image is the round front or back and whether the down image is the opposite (back or front image) automatically. This inherent support for either orientation round configuration is significant because it potentially doubles the throughput speed of the machine by eliminating fewer rounds at the top from the round feeding system.

Figure 29:
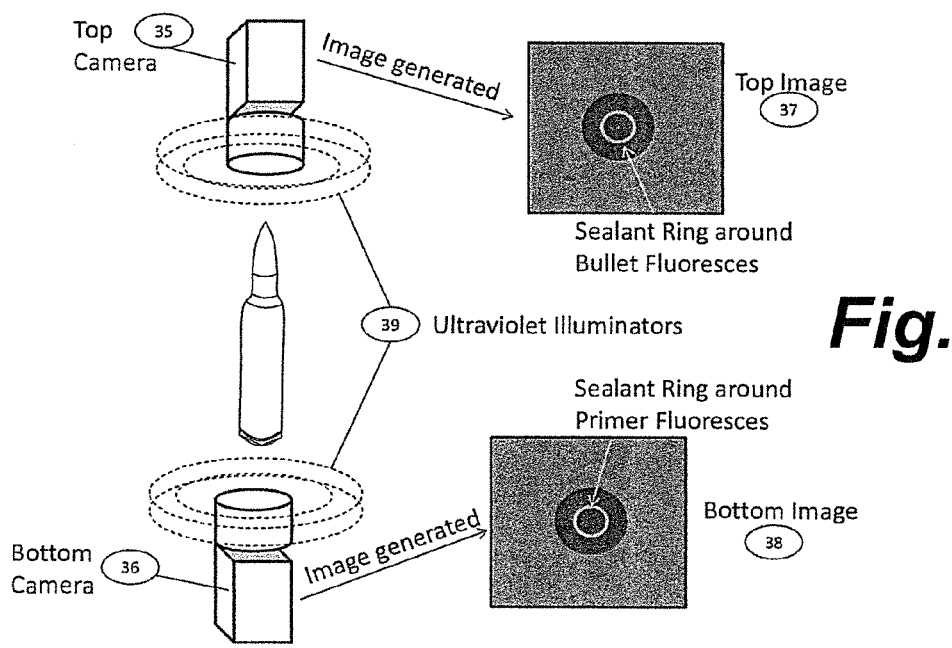
FIG. 29 shows a sealant check camera and illuminator.

The inspection head shown in FIG. 29 allows the system to check the round for properly applied sealant (identified by ultraviolet illumination (39), and top (35) and bottom (36) imaging). The ultraviolet light makes the sealant visible to the sealant inspection module. The tip (37) and mouth (38) interface is checked for properly applied sealant. This inspection is normally performed over a conveyor and may or may not require a triggering round present/absent sensor that is independent of the camera image captures.

Figure 30:
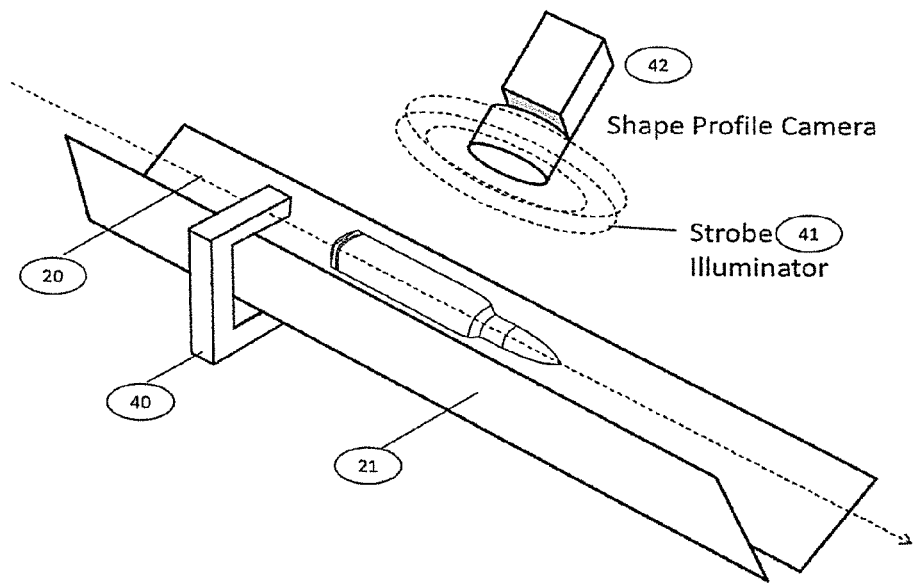
FIG. 30 depicts a secondary shape and outline camera and strobe.

The secondary strobe light illuminated area image capture unit of FIG. 30 may be added to more precisely measure certain shape profiles related parameters like round length, shoulder to tip parameters, shoulder angle, shoulder to head, etc. This unit uses a laser detector (40) to trigger as the round approaches the secondary shape capture station. Like the previously described tip/head stamp station, this station can process data from a front to back oriented round or a back to front oriented round and can adjust the time from trigger to strobe (41) and image capture (42) based on round, case or bullet type previously identified by earlier recognition modules.

Figure 31:
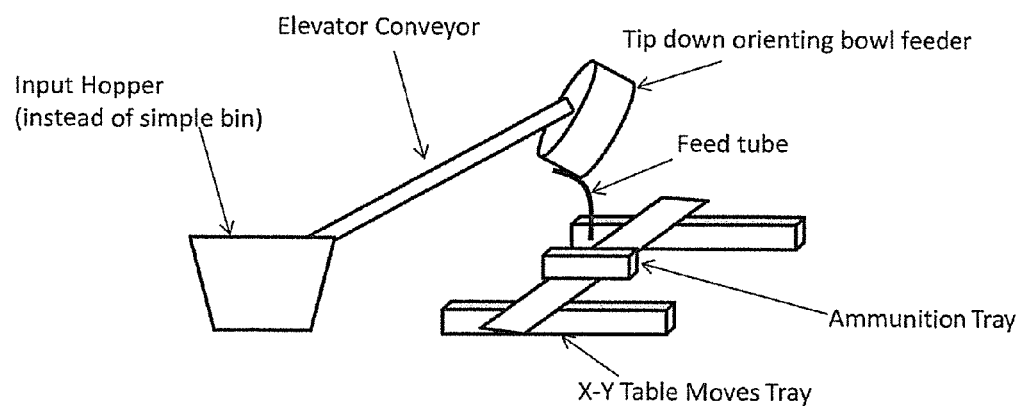
FIG. 31 illustrates feed into a round packaging machine instead of a bin.

Different versions of the inspection head provide for transferring unidentified or uninspected rounds back to the input feeder for re-inspection through a recycling conveyor ((19 & 20) in FIG. 20—recalculating conveyor). Other versions of the inspection head provide for transferring rounds to packaging machines instead of to type classified bins. This allows for rounds to be packed for resale or reuse individually as opposed to being packed in bulk in ammunition bids (FIG. 31).

We claim:

1. A method of inspecting and sorting munitions, ordnance or other manufactured parts, comprising the steps of:
consecutively conveying parts along a path which extends through a plurality of inspection stations including a circumference vision station;
facilitating movement of the parts through the circumference vision station such that all sides of each part are at least temporarily visually unobstructed;
illuminating an exterior side surface of each part when the part is visually unobstructed to generate a plurality of side images of the parts;
processing the side images of the part to identify physical part characteristics or defects; and
sorting the parts in accordance with the part characteristics or defects.

2. The method of claim 1, including the steps of:
directing parts identified as having an unacceptable defect to a defective part area; and
directing parts not identified as having an unacceptable defect to an acceptable part area.

3. The method of claim 1, including the step of generating at least two opposing side images of a part.

4. The method of claim 1, including the step of constructing a profile of a part based upon the multiple side images.

5. The method of claim 1, including the steps of:
storing a plurality of object templates;
processing the side images to generate length and profile information; and
determining part type by comparing the length and profile information to the stored templates.

6. The method of claim 1, including the steps of:
storing information relating to one or more known types of defects based on shape, material type, surface markings, letters or head stamps, or parts being unknown or having an uninspected status; and
processing the side images of each part to identify part characteristics or defects based upon the stored information.

7. The method of claim 1, including the steps of directing parts into one or more corresponding bins based upon part type, color, coding, or quality.

8. The method of claim 1, including the step of conveying a single, consecutive line or column of parts through a space having at least one continuous circumferential gap such that all sides of each object passing through the gap are visible for illumination and imaging.

9. The method of claim 1, including the step of conveying a single, consecutive line or column of parts down a v-channel such that each part accelerates at a predictable rate, the v-channel having one or more gaps facilitating illumination, imaging and profile capture on all sides.

10. The method of claim 1, wherein the side images of the part are acquired with line scan cameras or two-dimensional image sensors.

11. The method of claim 1, wherein the parts are illuminated with uniform ring illumination.

12. The method of claim 1, wherein the parts are illuminated with a strobe light.

13. The method of claim 1, including the step of generating side images that show part tip type, a model numbers or a lot number.

14. The method of claim 1, including the step of using one or more of the following to determine part type, material, lot or model number:
a) Barcode, machine-readable code or character recognition,
b) RFID,
c) Size profiling,
d) Shape analysis,
e) Hue or RBG color analysis, and
f) End marking identification.

15. The method of claim 1, including inspection stations that detect defects using one or more of the following:
a) Eddy current analysis,
b) Ultrasound analysis,
c) Laser spectroscopy for defect detection,
d) Laser interferometry,
e) Size profiling,
f) Shape analysis,
g) Hue or RBG color analysis for corrosion detection,
h) Intensity analysis, and
i) Gradient feature detection.

16. The method of claim 1, wherein:
the parts are rounds of ammunition; and
the method includes the step of using a tip color image of each round to locating tip and tip type coding.

17. The method of claim 1, including the step of using barcode, RFID, or character recognition to determine part end markings, if any.

18. A system for inspecting and sorting munitions, ordnance or other manufactured parts, comprising:
a feeder for consecutively conveying parts along a path which extends through a plurality of inspection stations;
the inspection stations including a circumference vision station through which each part is at least temporarily visually unobstructed;
an illumination assembly to illuminate a plurality of annular, exterior side surfaces of a part when the part is visually unobstructed;
an imaging assembly to generate a plurality of side images of the part when illuminated;
a processor for processing the side images to identify part characteristics or defects; and
a sorter for sorting the parts in accordance with the part characteristics or defects.

19. The system of claim 18, wherein the processor is operative to construct a profile of a part based upon the multiple side images.

20. The system of claim 18, further including:
a memory for storing a plurality of object templates; and
wherein the processor is operative to determine part type by comparing the length and profile information to the stored templates.

21. The system of claim 18, further including:
a memory for storing information relating to one or more known types of defects based on shape, material type, surface markings, letters or head stamps, or parts being unknown or having an uninspected status; and
wherein the processor is operative to identify part characteristics or defects based upon the stored information.

22. The system of claim 18, wherein the sorter includes one or more corresponding bins to receive parts based upon part type, color, coding, or quality.

23. The system of claim 18, wherein the feeder includes a conveyor for conveying a single, consecutive line or column of parts through a space having at least one continuous circumferential gap such that all sides of each object passing through the gap are visible for illumination and imaging.

24. The system of claim 18, including a vchannel conveyor through which parts in a single, consecutive line accelerate at a predictable rate, the vchannel having one or more gaps facilitating illumination, imaging and profile capture on all sides.

25. The system of claim 18, wherein the imaging assembly acquires side images of the part with line-scan cameras or two-dimensional image sensors.

26. The system of claim 18, wherein the illumination assembly is based upon uniform ring or strobe illumination.

27. The system of claim 18, wherein the processor is operative to process the side images to determine part tip type, model number or lot number.

28. The system of claim 18, further including one or more of the following to determine part type, material, lot or model number:
a) Barcode, machine-readable code or character recognition,
b) RFID,
c) Size profiling,
d) Shape analysis,
e) Hue or RBG color analysis, and
f) End marking identification.

29. The system of claim 18, further including one or more of the following to determine defects:

a) Eddy current analysis,
b) Ultrasound analysis,
c) Laser spectroscopy for defect detection,
d) Laser interferometry,
e) Size profiling,
f) Shape analysis,
g) Hue or RBG color analysis for corrosion detection,
h) Intensity analysis, and
i) Gradient feature detection.

30. The system of claim 18, wherein:
the parts are rounds of ammunition; and
further including a tip recognition module to generate a tip color image of each round to locate the tip and to determine tip type coding.

31. The system of claim 18, including barcode, RFID, or character recognition to determine part end markings, if any.

32. The system of claim 18, further including computer-controlled blow-off air jets to direct the defective part or part by type to a defective parts bin of type-specific bin by-passing other inspections.

33. The system of claim 18, wherein:
the parts are rounds of ammunition; and
the material of the casing or round is identified by color and/or texture.

34. The system of claim 18, wherein:
the parts are rounds of ammunition; and
the feeder accepts mix caliber ammunition.

35. The system of claim 18, wherein:
the parts are rounds of ammunition; and
the system allows tip first or head-end first ordering of the rounds to be inspected.

\* \* \* \* \*